(12) United States Patent
Sun et al.

(10) Patent No.: US 8,712,135 B2
(45) Date of Patent: Apr. 29, 2014

(54) APPARATUS AND METHOD FOR IMAGE RECONSTRUCTION AND CT SYSTEM

(75) Inventors: Zhihui Sun, Beijing (CN); Jiaqin Dong, Beijing (CN); Shuqin Dong, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 279 days.

(21) Appl. No.: 13/283,790

(22) Filed: Oct. 28, 2011

(65) Prior Publication Data

US 2012/0106818 A1    May 3, 2012

(30) Foreign Application Priority Data

Oct. 29, 2010   (CN) .......................... 2010 1 0530606

(51) Int. Cl.
*G06K 9/00*    (2006.01)

(52) U.S. Cl.
USPC ............... 382/131; 382/128; 382/132; 378/4; 378/9; 378/19

(58) Field of Classification Search
USPC ................... 382/128–131; 378/4, 15, 99, 901
See application file for complete search history.

(56) References Cited

U.S. PATENT DOCUMENTS

| | | | | |
|---|---|---|---|---|
| 6,263,096 | B1 * | 7/2001 | Boag et al. ..................... | 382/128 |
| 6,359,956 | B1 * | 3/2002 | Hsieh et al. ...................... | 378/15 |
| 6,452,996 | B1 * | 9/2002 | Hsieh ............................... | 378/15 |
| 6,873,676 | B2 * | 3/2005 | Hsieh ................................ | 378/4 |
| 7,062,009 | B2 * | 6/2006 | Karimi et al. ................... | 378/19 |
| 7,245,755 | B1 * | 7/2007 | Pan et al. ....................... | 382/131 |
| 7,324,623 | B2 * | 1/2008 | Heuscher .......................... | 378/9 |
| 7,693,318 | B1 * | 4/2010 | Stalling et al. ................ | 382/128 |
| 7,916,831 | B2 * | 3/2011 | Sun et al. ......................... | 378/19 |
| 8,031,829 | B2 * | 10/2011 | Yin et al. ........................... | 378/9 |
| 8,213,694 | B2 * | 7/2012 | Vaz et al. ...................... | 382/128 |
| 8,218,841 | B2 * | 7/2012 | Kadrmas ....................... | 382/128 |
| 8,326,011 | B2 * | 12/2012 | Star-Lack et al. ............. | 382/131 |
| 8,622,615 | B2 * | 1/2014 | Ren et al. ....................... | 378/207 |

(Continued)

FOREIGN PATENT DOCUMENTS

JP    2009268892 A   * 11/2009
JP    2012020121 A   *  2/2012

OTHER PUBLICATIONS

Ge Wang, "X-ray micro-CT with a displaced detector array", Medical Physics, Jun. 2002, 1634-1636, 29 (7).

*Primary Examiner* — Jayesh A Patel
*Assistant Examiner* — Iman K Kholdebarin
(74) *Attorney, Agent, or Firm* — Armstrong Teasdale LLP (57) ABSTRACT

A method for image reconstruction using projection data obtained by an asymmetric detector includes dividing the projection data into Regions 1, 2, 3, 4, and 5. Region 1 is an asymmetric region having detecting channels but no detecting channels symmetrical about a central channel. Region 2 is a transition region having detecting channels and there are detecting channels symmetrical about the central channel. Region 3 is a symmetric region having detecting channels and there are detecting channels symmetrical about the central channel. Region 4 is a transition region having detecting channels and there are detecting channels symmetrical about the central channel. Region 5 is a truncated region where there is no detecting channel. The method includes performing a view angle weighting on projection data in each of the five regions, and reconstructing a tomographic image of an irradiated subject from the weighted projection data.

18 Claims, 5 Drawing Sheets

(56) References Cited

U.S. PATENT DOCUMENTS

| | | |
|---|---|---|
| 2004/0165695 A1* | 8/2004 | Karimi et al. .................... 378/19 |
| 2006/0159220 A1* | 7/2006 | Heuscher ........................... 378/9 |
| 2007/0242868 A1* | 10/2007 | Stanton et al. ................. 382/131 |
| 2008/0292194 A1* | 11/2008 | Schmidt et al. ............... 382/217 |
| 2009/0110259 A1* | 4/2009 | Yin et al. ...................... 382/132 |
| 2009/0274266 A1* | 11/2009 | Sun et al. ........................ 378/19 |
| 2010/0121183 A1* | 5/2010 | Taguchi et al. ................ 600/427 |
| 2011/0110573 A1* | 5/2011 | Wiegert et al. ................ 382/131 |
| 2012/0012742 A1* | 1/2012 | Ren et al. .................... 250/252.1 |
| 2012/0014582 A1* | 1/2012 | Schaefer et al. .............. 382/131 |
| 2012/0106818 A1* | 5/2012 | Sun et al. ...................... 382/131 |
| 2012/0207370 A1* | 8/2012 | Fahimian et al. ............. 382/131 |
| 2012/0263360 A1* | 10/2012 | Zhu et al. ...................... 382/131 |
| 2013/0170722 A1* | 7/2013 | Star-Lack et al. ............. 382/131 |
| 2013/0195341 A1* | 8/2013 | Liu et al. ....................... 382/131 |

\* cited by examiner

APPARATUS AND METHOD FOR IMAGE RECONSTRUCTION AND CT SYSTEM

CROSS REFERENCE TO RELATED APPLICATIONS

This application claims the benefit of Chinese Patent Application No. 201010530606.8 filed Oct. 29, 2010, which is hereby incorporated by reference in its entirety.

BACKGROUND OF THE INVENTION

The embodiments described herein generally relate to the field of CT image reconstruction, and in particular to an apparatus and method for image reconstruction and CT system.

It is well-known that CT systems are having an increasing effect on medical diagnosis, because they can clearly image various organs of a patient so as to enable the doctors to easily identify the diseased region and to take corresponding measures of treatment. The assistance of CT systems in medical treatment has become a very important as well as an essential part in modern medicine.

Typically, a CT system includes a tube and a detector. The tube is used for emitting X-rays, and the detector is used for receiving the X-rays emitted by the tube and converting them into electrical signals to form projection data. Then, images of the irradiated subject (patient) are reconstructed according to the projection data.

The detector usually includes a symmetric detector and an asymmetric detector. The symmetric detector refers to a detector in which the numbers of detecting units at both sides of the central channel (a channel corresponding to the center of rotation) of the detector are equal or are different by no more than two channels. The asymmetric detector refers to a detector in which the numbers of detecting units at both sides of the central channel of the detector are unequal and are different by more than two channels.

The advent of the asymmetric detector in a CT system can either reduce the number of detecting units at one side of the central channel of the detector so as to reduce the cost, or increase the number of detecting units at one side of the central channel so as to enlarge the scan focus of view.

Compared to the symmetric detector, the projection data obtained by using the asymmetric detector have data loss at one side of the central channel, so the reconstruction method used for the projection data obtained by the symmetric detector is not applicable to the projection data obtained by the asymmetric detector. The reconstruction method for the projection data obtained by the asymmetric detector has, therefore, become one of the hotspots that are studied in the industry.

An article titled "X-ray micro-CT with a displaced detector array" by GE WANG published in Medical Physics, 29 (7): 1634-6 in June 2002 describes a method of reconstruction under an asymmetric detector in an axial scan. However, the reconstructed image cannot have an image quality similar to the original one in the central symmetric region under the asymmetric detector.

U.S. Pat. No. 6,873,676 and U.S. Pat. No. 6,452,996 disclose "convolution reconstruction algorithm for multi-slice CT" and "methods and apparatus utilizing generalized helical interpolation algorithm". These patents describe the convolution reconstruction algorithm/the generalized helical interpolation algorithm, which can better suppress noises and image artifacts as compared to other two-dimensional helical reconstruction algorithms, especially for the multi-row CT having more than four rows.

U.S. Pat. No. 7,062,009 describes dividing the projection data into a symmetric region and an asymmetric region. For projection data in the symmetric region, the helical interpolation weight adopts the complementary interpolation weight, while for the projection data in the asymmetric region, the helical interpolation weight adopts the direct interpolation weight. This patent describes the reconstruction method of a helical scan under the asymmetric detector in general terms, but the reconstructed image has a quality defect. Moreover, this patent fails to provide a solution to image reconstruction for multi-row CT having more than four rows.

SUMMARY OF THE INVENTION

The main technical problem to be solved by the embodiments described herein is to provide an apparatus and method for image reconstruction that can make the quality of the image reconstructed from projection data obtained by the asymmetric detector to be the same as the quality of the image reconstructed from projection data obtained by the symmetric detector as well as a CT system.

According to one aspect, a method for image reconstruction is provided, which is used for image reconstruction according to projection data obtained by the asymmetric detector. The method includes dividing projection data into five regions: Region 1, Region 2, Region 3, Region 4 and Region 5. Region 1 is an asymmetric region where there are detecting channels but no detecting channels symmetrical about the central channel. Region 2 is a transition region where there are detecting channels, and there are also detecting channels symmetrical about the central channel. Region 3 is a symmetric region where there are detecting channels and there are also detecting channels symmetrical about the central channel. Region 4 is a transition region where there are detecting channels and there are also detecting channels symmetrical about the central channel. Region 5 is a truncated region where there are no detecting channels. The method further includes performing a view angle weighting on projection data in each of the five regions, and reconstructing the tomographic image of the irradiated subject from weighted projection data.

For the axial scan, the weights of projection data in the five regions are as follows: the weights of projection data in Region 1 are 1; the weights of projection data in Region 3 are ½; the weights of projection data in Region 5 are 0; the weights of projection data in the Region 2 are 1~½; and the weights of projection data in Region 4 are ½~0.

The weights of projection data in Region 2 are obtained from the following formula:

$$w(\gamma) = 1 - \frac{1}{2} * trans\left(\gamma, -\gamma_0 + \frac{\Delta\gamma}{2}, \Delta\gamma\right),$$

wherein $w(\gamma)$ represents the weight of projection data obtained when the fan angle is $\gamma$; $\gamma_0$ represents the largest fan angle at the small fan angle side; $\Delta\gamma$ represents the width of the transition region;

$$trans\left(\gamma, -\gamma_0 + \frac{\Delta\gamma}{2}, \Delta\gamma\right),$$

is the transition function. Suppose $\Delta\gamma=b$ and $$-\gamma_0 + \frac{\Delta\gamma}{2} = a,$$

then, $$trans(\gamma, a, b) = f\left(\frac{\gamma - \left(a - \frac{b}{2}\right)}{b}\right) = f(x)$$

wherein, $f(x)$ is a differentiable function, and when its independent variable varies from 0 to 1, the function value varies from 0 to 1 and satisfies $f(x)+f(1-x)=1$.

The weights of projection data in 4 are obtained from the following formula:

$$w(\gamma) = \frac{1}{2} - \frac{1}{2} * trans\left(\gamma, \gamma_0 - \frac{\Delta\gamma}{2}, \Delta\gamma\right).$$

For the helical scan, the weights of projection data in the five regions are as follows: the weights of projection data in Region 5 are 0; and the weights of projection data in the remaining four regions are:

$$\xi(\gamma, \beta, i) = \sum_{n=0}^{N-k} \alpha(n) w_n(\gamma, \beta, i)$$

wherein, $\xi(\gamma,\beta,i)$ represents the weight of projection data at the position of fan angle $\gamma$ in the $i^{th}$ row of the asymmetric detector under the view angle $\beta$; N represents the number of rows of the asymmetric detector, k represents consecutive k rows in the asymmetric detector and k=p, p represents the pitch, a(n) represents the weight of subset n and $\Sigma a(n)=1$, and $w_n(\gamma,\beta,i)$ represents, in subset n, the weight of projection data at the position of fan angle $\gamma$ in the $i^{th}$ row of the asymmetric detector under the view angle $\beta$.

For Region 3 and Region 1:

$$w_n(\gamma, \beta, i) =$$

$$\begin{cases} \sum_{m=1}^{M} \frac{\lambda_{n,m} * (\beta - \theta_{n,m-}(\gamma, \beta, i))}{\theta_{n,m}(\gamma, \beta, i) - \theta_{n,m-}(\gamma, \beta, i)}, & \theta_{n,m-}(\gamma, \beta, i) \le \beta < \theta_{n,m}(\gamma, \beta, i) \\ \sum_{m=1}^{M} \frac{\lambda_{n,m} * (\theta_{n,m+}(\gamma, \beta, i) - \beta)}{\theta_{n,m+}(\gamma, \beta, i) - \theta_{n,m}(\gamma, \beta, i)}, & \theta_{n,m}(\gamma, \beta, i) \le \beta < \theta_{n,m+}(\gamma, \beta, i) \\ 0, & \text{otherwise,} \end{cases}$$

wherein, $\lambda_{n,m}$ represents the weight in the $n^{th}$ subset with the $m^{th}$ kind of interpolation; $\theta_{n,m}(\gamma,\beta,i)$ represents the center of view angle when calculating the weight $w_n(\gamma,\beta,i)$ in the $n^{th}$ subset under the $m^{th}$ kind of interpolation, and the weight thereof is 1; $\theta_{n,m-}(\gamma,\beta,i)$ represents the lower boundary of the view angle when calculating $w_n(\gamma,\beta,i)$ under the $m^{th}$ kind of interpolation, and the weight there of is 0; and $\theta_{n,m+}(\gamma,\beta,i)$ represents the upper boundary of the view angle when calculating $w_n(\gamma,\beta,i)$ under the $m^{th}$ kind of interpolation, and the weight there of is 0.

For 3:

$$\theta_{n,m-}(\gamma, \beta, i) = \phi_{i,m} - \frac{\pi}{p} - (2 - \delta_m) * \gamma,$$

$$\theta_{n,m+}(\gamma, \beta, i) = \phi_{i,m} + \frac{\pi}{p} - (2 - \delta_m) * \gamma,$$

$$\theta_{n,m}(\gamma, \beta, i) = \phi_{i,m} - \delta_m * \gamma$$

wherein, $$\phi_{i,m} = \frac{2i\pi}{p},$$

$\phi_{i,m}$ represents the center of a view angle of the central channel in the $i^{th}$ row; and $\delta_m$ is the inclined slop of the $m^{th}$ kind of interpolation.

For Region 1:

$$\theta_{n,m}(\gamma, \beta, i) = \theta_{n,m}(-\gamma_0 + \Delta\gamma, \beta, i) = \phi_{i,m} - \delta_m * (-\gamma_0 + \Delta\gamma)$$

$$\theta_{n,m-}(\gamma, \beta, i) = \theta_{n,m}(-\gamma_0 + \Delta\gamma, \beta, i) - \frac{2\pi}{p}$$

$$= \phi_{i,m} - \delta_m * (-\gamma_0 + \Delta\gamma) - \frac{2\pi}{p},$$

$$\theta_{n,m+}(\gamma, \beta, i) = \theta_{n,m}(-\gamma_0 + \Delta\gamma, \beta, i) + \frac{2\pi}{p}$$

$$= \phi_{i,m} - \delta_m * (-\gamma_0 + \Delta\gamma) + \frac{2\pi}{p}$$

wherein $\gamma_0$ represents the largest fan angle at the small fan angle side; and $\Delta\gamma$ represents the width of the transition region.

For Region 2:

$$w_n(\gamma, \beta, i) = w_n(-\gamma_0, \beta, i) +$$

$$(w_n(-\gamma_0 + \Delta\gamma, \beta, i) - w_n(-\gamma_0, \beta, i)) * trans\left(\gamma, -\gamma_0 + \frac{\Delta\gamma}{2}, \Delta\gamma\right)$$

wherein, $$trans\left(\gamma, -\gamma_0 + \frac{\Delta\gamma}{2}, \Delta\gamma\right)$$

is the transition function. Suppose $\Delta\gamma=b$ and $$-\gamma_0 + \frac{\Delta\gamma}{2} = a,$$

then, $$\text{trans}(\gamma, a, b) = f\left(\frac{\gamma - \left(a - \frac{b}{2}\right)}{b}\right) = f(x)$$

wherein, $f(x)$ is a differentiable function and when its independent variable varies from 0 to 1, the function value varies from 0 to 1 and satisfies $f(x)+f(1-x)=1$.

For Region 4:

$$w_n(\gamma, \beta, i) =$$

$$w_n(\gamma_0 - \Delta\gamma, \beta + 2*(\gamma - \gamma_0 + \Delta\gamma), i) * \left(1 - \text{trans}\left(\gamma, \gamma_0 - \frac{\Delta\gamma}{2}, \Delta\gamma\right)\right).$$

According to another aspect, an apparatus for image reconstruction is provided, which is used for image reconstruction according to projection data obtained by the asymmetric detector. The apparatus includes a region dividing unit for dividing projection data into five regions: Region 1, Region 2, Region 3, Region 4 and Region 5. Region 1 is an asymmetric region where there are detecting channels but no detecting channels symmetrical about the central channel. Region 2 is a transition region where there are detecting channels and there are also detecting channels symmetrical about the central channel. Region 3 is a symmetric region where there are detecting channels and there are also detecting channels symmetrical about the central channel. Region 4 is a transition region where there are detecting channels and there are also detecting channels symmetrical about the central channel. Region 5 is a truncated region where there are no detecting channels. The apparatus further includes a view angle weighting unit for performing a view angle weighting on projection data in each of the five regions; and a reconstructing unit for reconstructing the tomographic image of the irradiated subject from weighted projection data:

For the axial scan, the weights of projection data in the five regions are as follows: the weights of projection data in Region 1 are 1; the weights of projection data in Region 3 are ½; the weights of projection data in Region 5 are 0; the weights of projection data in Region 2 are 1~½; and the weights of projection data in Region 4 are ½~0.

The weights of projection data in Region 2 are obtained from the following formula:

$$w(\gamma) = 1 - \frac{1}{2} * \text{trans}\left(\gamma, -\gamma_0 + \frac{\Delta\gamma}{2}, \Delta\gamma\right)$$

wherein, $w(\gamma)$ represents the weight of projection data obtained when the fan angle is $\gamma$; $\gamma_0$ represents the largest fan angle at the small fan angle side; $\Delta\gamma$ represents the width of the transition region; and $$\text{trans}\left(\gamma, -\gamma_0 + \frac{\Delta\gamma}{2}, \Delta\gamma\right)$$

is the transition function. Suppose $\Delta\gamma=b$ and $$-\gamma_0 + \frac{\Delta\gamma}{2} = a,$$

then, $$\text{trans}(\gamma, a, b) = f\left(\frac{\gamma - \left(a - \frac{b}{2}\right)}{b}\right) = f(x)$$

wherein, $f(x)$ is a differentiable function, and when its independent variable varies from 0 to 1, the function value varies from 0 to 1 and satisfies $f(x)+f(1-x)=1$.

The weights of projection data in Region 4 are obtained from the following formula:

$$w(\gamma) = \frac{1}{2} - \frac{1}{2} * \text{trans}\left(\gamma, \gamma_0 - \frac{\Delta\gamma}{2}, \Delta\gamma\right)$$

$$\text{trans}\left(\gamma, \gamma_0 - \frac{\Delta\gamma}{2}, \Delta\gamma\right)$$

is the transition function. Suppose $\Delta\gamma=b$ and $$\gamma_0 - \frac{\Delta\gamma}{2} = a,$$

then, $$\text{trans}(\gamma, a, b) = f\left(\frac{\gamma - \left(a - \frac{b}{2}\right)}{b}\right) = f(x)$$

wherein, $f(x)$ is a differentiable function, and when its independent variable varies from 0 to 1, the function value varies from 0 to 1 and satisfies $f(x)+f(1-x)=1$.

For the helical scan, the weights of projection data in the five regions are as follows: the weights of projection data in Region 5 are 0; and the weights of projection data in the remaining four regions are:

$$\xi(\gamma, \beta, i) = \sum_{n=0}^{N-k} \alpha(n) w_n(\gamma, \beta, i)$$

wherein, $\xi(\gamma,\beta,i)$ represents the weight of projection data at the position of a fan angle $\gamma$ in the $i^{th}$ row of the asymmetric detector under the view angle $\beta$;

N represents the number of rows of the asymmetric detector, k represents consecutive k rows in the asymmetric detector and k=p, p represents the pitch, a(n) represents the weight of subset n and $\Sigma a(n)=1$, $w_n(\gamma,\beta,i)$ represents, in subset n, the weight of projection data at the position of fan angle $\gamma$ in the $i^{th}$ row of the asymmetric detector under the view angle $\beta$.

For Region 3 and Region 1:

$$w_n(\gamma, \beta, i) = \begin{cases} \sum_{m=1}^{M} \frac{\lambda_{n,m} * (\beta - \theta_{n,m-}(\gamma, \beta, i))}{\theta_{n,m}(\gamma, \beta, i) - \theta_{n,m-}(\gamma, \beta, i)}, & \theta_{n,m-}(\gamma, \beta, i) \leq \beta < \theta_{n,m}(\gamma, \beta, i) \\ \sum_{m=1}^{M} \frac{\lambda_{n,m} * (\theta_{n,m+}(\gamma, \beta, i) - \beta)}{\theta_{n,m+}(\gamma, \beta, i) - \theta_{n,m}(\gamma, \beta, i)}, & \theta_{n,m}(\gamma, \beta, i) \leq \beta < \theta_{n,m+}(\gamma, \beta, i) \\ 0, & \text{otherwise,} \end{cases}$$

wherein, $\lambda_{n,m}$ represents the weight in the $n^{th}$ subset with the $m^{th}$ kind of interpolation; $\theta_{n,m}(\gamma,\beta,i)$ represents the center of view angle when calculating the weight $w_n(\gamma,\beta,i)$ in the $n^{th}$ subset under the $m^{th}$ kind of interpolation, and the weight thereof is 1; $\theta_{n,m-}(\gamma,\beta,i)$ represents the lower boundary of the view angle when calculating $(\gamma,\beta,i)$ under the $m^{th}$ kind of interpolation, and the weight there of is 0; and $\theta_{n,m+}(\gamma,\beta,i)$ represents the upper boundary of the view angle when calculating $w_n(\gamma,\beta,i)$ under the $m^{th}$ kind of interpolation, and the weight thereof is 0.

For Region 3:

$$\theta_{n,m-}(\gamma, \beta, i) = \phi_{i,m} - \frac{\pi}{p} - (2 - \delta_m) * \gamma,$$

$$\theta_{n,m+}(\gamma, \beta, i) = \phi_{i,m} + \frac{\pi}{p} - (2 - \delta_m) * \gamma,$$

$$\theta_{n,m}(\gamma, \beta, i) = \phi_{i,m} - \delta_m * \gamma$$

wherein, $$\phi_{i,m} = \frac{2i\pi}{p},$$

$\phi_{i,m}$ represents the center of view angle of the central channel in the $i^{th}$ row; and $\delta_m$ is the inclined slop of the $m^{th}$ kind of interpolation.

For Region 1:

$$\theta_{n,m}(\gamma, \beta, i) = \theta_{n,m}(-\gamma_0 + \Delta\gamma, \beta, i) = \phi_{i,m} - \delta_m * (-\gamma_0 + \Delta\gamma)$$

$$\theta_{n,m-}(\gamma, \beta, i) = \theta_{n,m}(-\gamma_0 + \Delta\gamma, \beta, i) - \frac{2\pi}{p}$$

$$= \phi_{i,m} - \delta_m * (-\gamma_0 + \Delta\gamma) - \frac{2\pi}{p},$$

$$\theta_{n,m+}(\gamma, \beta, i) = \theta_{n,m}(-\gamma_0 + \Delta\gamma, \beta, i) + \frac{2\pi}{p}$$

$$= \phi_{i,m} - \delta_m * (-\gamma_0 + \Delta\gamma) + \frac{2\pi}{p}$$

wherein $\gamma_0$ represents the largest fan angle at the small fan angle side; and $\Delta\gamma$ represents the width of the transition region.

For Region 2:

$$w_n(\gamma, \beta, i) = w_n(-\gamma_0, \beta, i) +$$

$$(w_n(-\gamma_0 + \Delta\gamma, \beta, i) - w_n(-\gamma_0, \beta, i)) * \text{trans}\left(\gamma, -\gamma_0 + \frac{\Delta\gamma}{2}, \Delta\gamma\right)$$

wherein, $$\text{trans}\left(\gamma, -\gamma_0 + \frac{\Delta\gamma}{2}, \Delta\gamma\right)$$

is the transition function. Suppose $\Delta\gamma = b$ and $$-\gamma_0 + \frac{\Delta\gamma}{2} = a,$$

then, $$\text{trans}(\gamma, a, b) = f\left(\frac{\gamma - \left(a - \frac{b}{2}\right)}{b}\right) = f(x)$$

wherein, $f(x)$ is a differentiable function and when its independent variable varies from 0 to 1, the function value varies from 0 to 1 and satisfies $f(x)+f(1-x)=1$.

For Region 4:

$$w_n(\gamma, \beta, i) =$$

$$w_n(\gamma_0 - \Delta\gamma, \beta + 2*(\gamma - \gamma_0 + \Delta\gamma), i) * \left(1 - \text{trans}\left(\gamma, \gamma_0 + \frac{\Delta\gamma}{2}, \Delta\gamma\right)\right).$$

According to yet another aspect, a CT system is provided, which includes the apparatus for image reconstruction described above.

Compared to the prior art, the apparatus and method for image reconstruction and the CT system have the following advantageous effects.

First, the embodiments described herein divide projection data into five regions and perform a view angle weighting on projection data in each region, so that the quality of the image reconstructed from projection data obtained by the asymmetric detector is the same as the quality of the image reconstructed from projection data obtained by the symmetric detector.

Second, for the axial scan, the embodiments described herein employ the same way of weighting as that adopted by the symmetric detector in most of the regions of the central symmetric portion, so that the quality of the image reconstructed from the central regions is substantially the same as the quality of image when using a symmetrical detector.

Third, for the helical scan, the embodiments described herein incorporate the convolution reconstruction algorithm/generalized helical interpolation algorithm, so that most of the central symmetric portions have better noise characteristics, and the span of a single slice reconstructed region is reduced in the axial direction to the greatest extent, especially for a multi-row CT having more than four rows.

Finally, the embodiments described herein perform view angle weighting instead of projection data restoration, so the reconstruction time is basically not increased.

BRIEF DESCRIPTION OF THE DRAWINGS

To a more thorough understanding of the disclosure of the present invention, reference is below made to the descriptions taken in conjunction with the drawings, wherein.

DETAILED DESCRIPTION OF THE INVENTION

The specific embodiments of the present invention will be described in detail below, but the present invention is not limited to said specific embodiments.

Figure 1:
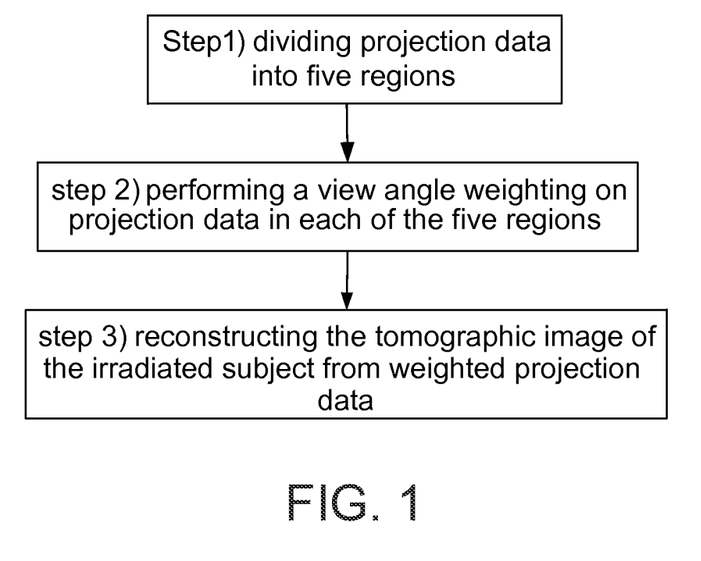
FIG. 1 illustrates a flow chart of an exemplary method for image reconstruction.

According to one aspect, a method for image reconstruction is disclosed, which is used for image reconstruction according to the projection data obtained by the asymmetric detector. As shown in FIG. 1, method includes dividing projection data into five regions: Region 1, Region 2, Region 3, Region 4 and Region 5. Region 1 is an asymmetric region where there are detecting channels but no detecting channels symmetrical about the central channel. Region 2 is a transition region where there are detecting channels, and there are also detecting channels symmetrical about the central channel. Region 3 is a symmetric region where there are detecting channels, and there are also detecting channels symmetrical about the central channel. Region 4 is a transition region where there are detecting channels, and there are also detecting channels symmetrical about the central channel. Region 5 is a truncated region where there is no detecting channel. The method further includes performing the view angle weighting on projection data in each of the five regions, and reconstructing the tomographic image of the irradiated subject from weighted projection data.

Figure 2:
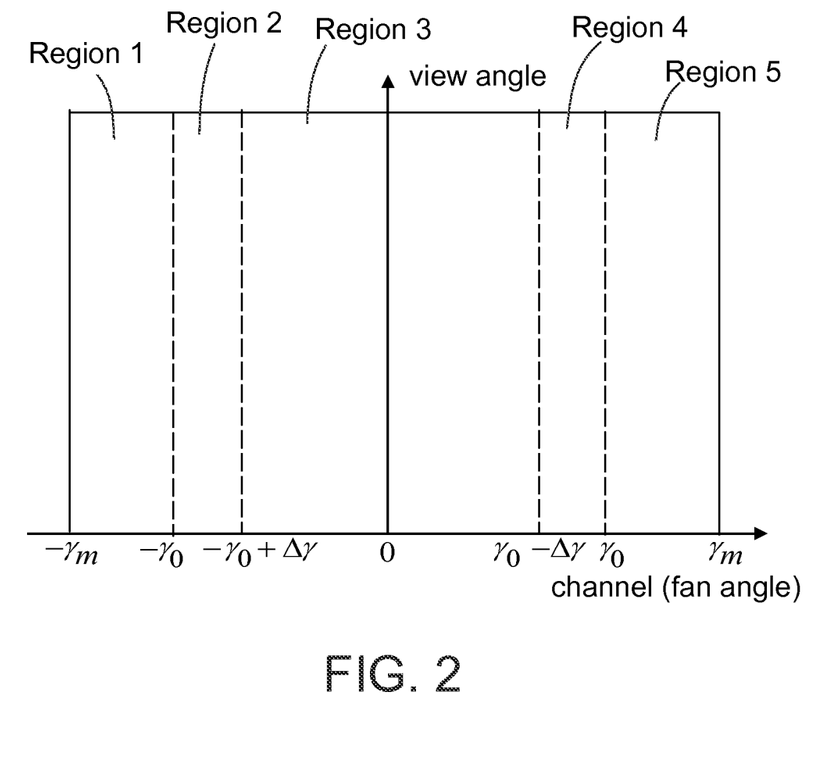
FIG. 2 illustrates a schematic diagram of division of the five regions of projection data.

It can be seen from the above that the method for image reconstruction is to divide projection data into five regions (as shown in FIG. 2), perform a view angle weighting for each of the regions, and then reconstruct the tomographic image of the irradiated subject from weighted projection data, so that the quality of the image reconstructed from projection data obtained by the asymmetric detector is the same as the quality of the image reconstructed from projection data obtained by the symmetric detector.

As shown in FIG. 2, $\gamma_m$ is the largest fan angle of the system (i.e. the largest fan angle at the large fan angle side), $\gamma_0$ is the largest fan angle at the small fan angle side, and $\Delta\gamma$ is the width of the transition region. In FIG. 2, the range of Region 1 is $-\gamma_m \leq \gamma \leq -\gamma_0$; the range of Region 2 is $-\gamma_0 < \gamma < -\gamma_0 + \Delta\gamma$; the range of Region 3 is $-\gamma_0 + \Delta\gamma \leq \gamma \leq \gamma_0 - \Delta\gamma$; the range of Region 4 is $\gamma_0 - \Delta\gamma < \gamma < \gamma_0$; and the range of Region 5 is $\gamma_0 \leq \gamma \leq \gamma_m$.

The width of the transition region is generally not less than 20 channels.

In terms of the way of scanning the subject, there are axial scans and helical scans. The axial scan means that the table of the CT system does not move axially when scanning to obtain a CT tomography. The helical scan means that the table of the CT system moves axially with uniform speed when scanning to obtain a CT tomography.

For the axial scan, the weights of projection data in the five regions are as follows: the weights of projection data in Region 1 are 1; the weights of projection data in Region 3 are ½; the weights of projection data in Region 5 are 0; the weights of projection data in Region 2 are 1~½; and the weights of projection data in Region 4 are ½~0.

The weights of projection data in Region 2 can be obtained from the following formula:

$$w(\gamma) = 1 - \frac{1}{2} * \text{trans}\left(\gamma, -\gamma_0 + \frac{\Delta\gamma}{2}, \Delta\gamma\right)$$

wherein $w(\gamma)$ represents the weight of projection data obtained when the fan angle is $\gamma$; and $$\text{trans}\left(\gamma, -\gamma_0 + \frac{\Delta\gamma}{2}, \Delta\gamma\right)$$

is the transition function. Suppose $\Delta\gamma = b$ and $$-\gamma_0 + \frac{\Delta\gamma}{2} = a,$$

then, $$\text{trans}(\gamma, a, b) = f\left(\frac{\gamma - \left(a - \frac{b}{2}\right)}{b}\right), \text{ and } f(x) = 3*x^2 - 2*x^3.$$

This is merely an example of the transition function. As for the definition of $f(x)$, in addition to $f(x) = 3*x^2 - 2*x^3$, any differentiable function is applicable as long as the function value of the differentiable function varies from 0 to 1 when its independent variable varies from 0 to 1 and $f(x) + f(1-x) = 1$ is satisfied.

When the axial scan is employed, the weights of projection data in Region 4 can be obtained from the following formula:

$$w(\gamma) = \frac{1}{2} - \frac{1}{2} * \text{trans}\left(\gamma, \gamma_0 - \frac{\Delta\gamma}{2}, \Delta\gamma\right).$$

Suppose $\Delta\gamma = b$ and $$\gamma_0 - \frac{\Delta\gamma}{2} = a,$$

then, $$\text{trans}(\gamma, a, b) = f\left(\frac{\gamma - \left(a - \frac{b}{2}\right)}{b}\right), \text{ and } f(x) = 3*x^2 - 2*x^3$$

wherein $\text{trans}\left(\gamma, \gamma_0 - \frac{\Delta\gamma}{2}, \Delta\gamma\right)$ is a transition function.

This is merely an example of the transition function. As for the definition of $f(x)$, in addition to $f(x) = 3*x^2 - 2*x^3$, any differentiable function is applicable as long as the function value of the differentiable function varies from 0 to 1 when its independent variable varies from 0 to 1 and $f(x)+f(1-x)=1$ is satisfied.

The process of performing image reconstruction using the method for image reconstruction described herein under an axial scan is described below through a specific example.

Figure 3:
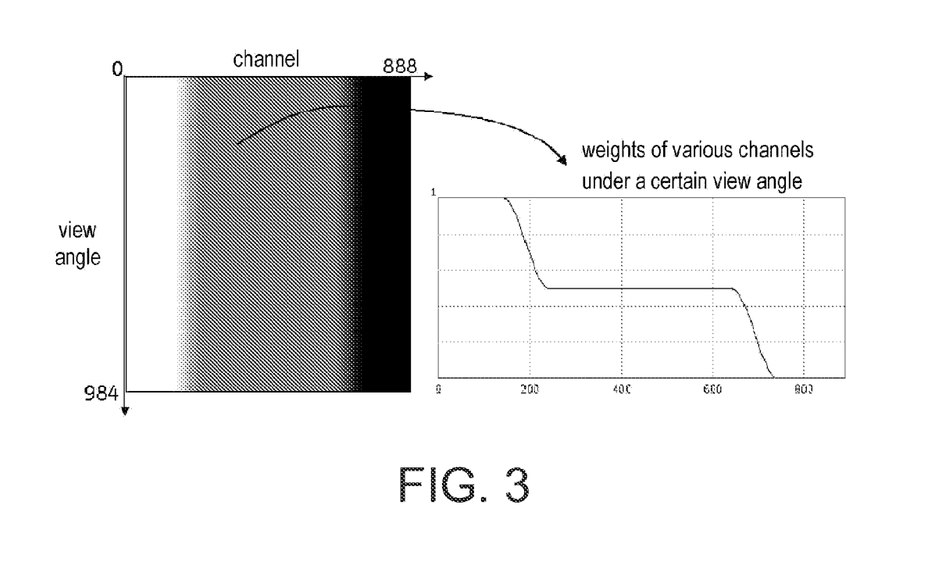
FIG. 3 illustrates a schematic diagram of the weights of the asymmetric reconstruction in an axial scan.

For example, one side of the asymmetric detector used has 444 channels, and the other side thereof has 300 channels, so the two sides are asymmetrical. The projection data obtained through the asymmetric detector are divided into five regions using the axial scan, as shown in FIG. 2. In this example, $\gamma_m$ is 27.4 degrees, $\gamma_0$ is 18.5 degrees, and $\Delta\gamma$ is 6.2 degrees. Then, the view angle weighting is performed on projection data in each of the five regions according to the above-mentioned formula, and the weights of the 888 channels at 984 view angles are calculated, as shown in FIG. 3. Finally, the tomographic image of the irradiated subject is reconstructed according to the weighted projection data. Reconstruction of the tomographic image of the irradiated subject according to the weighted projection data can be performed in any way known to those skilled in the art, and since it is the existing technique, no detailed description will be given here.

As shown in FIG. 3, the weights of the 888 channels at 984 view angles are in the left side, the weights of the 888 channels at one of the view angles are in the right side. The weight of each channel is independent of the view angle, so for any view angle, the obtained corresponding relationship between the weights and the channel remains the same.

Figure 4:
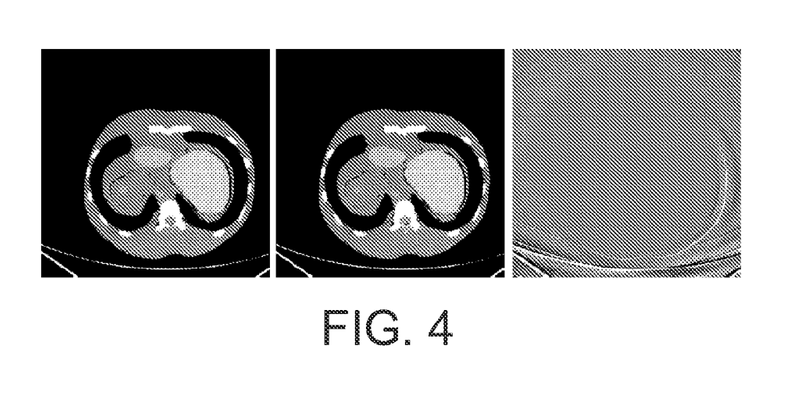
FIG. 4 illustrates a schematic diagram of the result of the reconstruction in an axial scan.

As shown in FIG. 4, the leftmost part is the image reconstructed by the symmetric detector, the middle part is the image reconstructed by the asymmetric detector using the method for image reconstruction described herein, and the rightmost part is the image of the difference image of the two images. The left two images have a window width of 200 and a window level of 60; and the rightmost image has a window width of 40 and a window level of 0. The centers of all images are in the center of scan.

As can be seen from FIG. 4, the image (the middle image) reconstructed by the method for image reconstruction described herein has almost the same quality in the central region as the image reconstructed by the symmetric detector.

The above describes the method of reconstructing the tomographic image of the irradiated subject through the projection obtained by the asymmetric detector with an axial scan. Next, the circumstances in a helical scan will be described.

For the helical scan, the weights of the projection data in the five regions are as follows: the weights of the projection data in Region 5 are 0 and the weights of the projection data in the remaining four regions are:

$$\xi(\gamma, \beta, i) = \sum_{n=0}^{N-k} \alpha(n) w_n(\gamma, \beta, i)$$

wherein, $\xi(\gamma,\beta,i)$ represents the weight of the projection data at the position of fan angle $\gamma$ in the $i^{th}$ row of the asymmetric detector under the view angle $\beta$;

N represents the number of rows of the asymmetric detector, k represents consecutive k rows in the asymmetric detector and k=p, p represents the pitch, a(n) represents the weight of subset n and the value of a(n) should guarantee that $$\sum_{n=0}^{N-k} \alpha(n) = 1,$$

for example, $$a(n) = \frac{1}{N-k+1},$$

$w_n(\gamma,\beta,i)$ represents, in subset n, the weight of the projection data at the position of fan angle $\gamma$ in the $i^{th}$ row of the asymmetric detector under the view angle $\beta$. The N rows of data are divided into N−k+1 subsets here, i.e. the first to the $k^{th}$ rows are subset 0; the second to the $(k+1)^{th}$ rows are subset 1; ... ; the $(N-k)^{th}$ to the $(N-1)^{th}$ rows are subset N−k−1; and the $(N-k+1)^{th}$ to the $N^{th}$ rows are subset N−k. k rows of data are used in each subset.

For Region 3 and Region 1:

$$w_n(\gamma, \beta, i) = \begin{cases} \sum_{m=1}^{M} \frac{\lambda_{n,m} * (\beta - \theta_{n,m-}(\gamma, \beta, i))}{\theta_{n,m}(\gamma, \beta, i) - \theta_{n,m-}(\gamma, \beta, i)}, & \theta_{n,m-}(\gamma, \beta, i) \leq \beta < \theta_{n,m}(\gamma, \beta, i) \\ \sum_{m=1}^{M} \frac{\lambda_{n,m} * (\theta_{n,m+}(\gamma, \beta, i) - \beta)}{\theta_{n,m+}(\gamma, \beta, i) - \theta_{n,m}(\gamma, \beta, i)}, & \theta_{n,m}(\gamma, \beta, i) \leq \beta < \theta_{n,m+}(\gamma, \beta, i) \\ 0, & \text{otherwise,} \end{cases}$$

wherein, M represents that there are M kinds of interpolation, each corresponding to a slope $\delta_m$ in a different reconstructed region; $\lambda_{n,m}$ represents the weight in the $n^{th}$ subset with the $m^{th}$ kind of interpolation, and the value of $\lambda_{n,m}$ should meet $$\sum_{m=1}^{M} \lambda_{n,m} = 1,$$

e.g.

$$\lambda_{n,m} = \frac{1}{M}; \theta_{n,m}(\gamma, \beta, i)$$

represents the center of view angle when calculating the weight $w_n(\gamma,\beta,i)$ in the $n^{th}$ subset under the $m^{th}$ kind of interpolation, and the weight thereof is 1; $\theta_{n,m-}(\gamma,\beta,i)$ represents the lower boundary of the view angle when calculating $w_n(\gamma,\beta,i)$ under the $m^{th}$ kind of interpolation, and the weight thereof is 0; and $\theta_{n,m+}(\gamma,\beta,i)$ represents the upper boundary of the view angle when calculating $w_n(\gamma,\beta,i)$ under the $m^{th}$ kind of interpolation, and the weight thereof is 0.

For Region 3:

$$\theta_{n,m-}(\gamma, \beta, i) = \phi_{i,m} - \frac{\pi}{p} - (2 - \delta_m) * \gamma,$$

$$\theta_{n,m+}(\gamma, \beta, i) = \phi_{i,m} + \frac{\pi}{p} - (2 - \delta_m) * \gamma,$$

$$\theta_{n,m}(\gamma, \beta, i) = \phi_{i,m} - \delta_m * \gamma$$

wherein, $$\phi_{i,m} = \frac{2i\pi}{p},$$

$\phi_{i,m}$ represents the center of view angle of the central channel in the $i^{th}$ row; and $\delta_m$ is the inclined slope of the $m^{th}$ kind of interpolation.

For Region 1:

$$\theta_{n,m}(\gamma, \beta, i) = \theta_{n,m}(-\gamma_0 + \Delta\gamma, \beta, i)$$
$$= \phi_{i,m} - \delta_m * (-\gamma_0 + \Delta\gamma)$$

$$\theta_{n,m-}(\gamma, \beta, i) = \theta_{n,m}(-\gamma_0 + \Delta\gamma, \beta, i) - \frac{2\pi}{p}$$
$$= \theta_{i,m} - \delta_m * (-\gamma_0 + \Delta\gamma) - \frac{2\pi}{p},$$

$$\theta_{n,m+}(\gamma, \beta, i) = \theta_{n,m}(-\gamma_0 + \Delta\gamma, \beta, i) + \frac{2\pi}{p}$$
$$= \phi_{i,m} - \delta_m * (-\gamma_0 + \Delta\gamma) + \frac{2\pi}{p}$$

wherein $\gamma_0$ represents the largest fan angle at the small fan angle side; and $\Delta\gamma$ represents the width of the transition region.

For Region 2:

$$w_n(\gamma, \beta, i) = w_n(-\gamma_0, \beta, i) +$$
$$(w_n(-\gamma_0 + \Delta\gamma, \beta, i) - w_n(-\gamma_0, \beta, i)) * trans\left(\gamma, -\gamma_0 + \frac{\Delta\gamma}{2}, \Delta\gamma\right)$$

wherein, $$trans\left(\gamma, -\gamma_0 + \frac{\Delta\gamma}{2}, \Delta\gamma\right)$$

is the transition function. Suppose $\Delta\gamma = b$ and $$-\gamma_0 + \frac{\Delta\gamma}{2} = a,$$

then, $$trans(\gamma, a, b) = f\left(\frac{\gamma - \left(a - \frac{b}{2}\right)}{b}\right), \text{ and } f(x) = 3*x^2 - 2*x^3$$

For Region 4:

$$w_n(\gamma, \beta, i) =$$
$$w_n(\gamma_0 - \Delta\gamma, \beta + 2*(\gamma - \gamma_0 + \Delta\gamma), i) * \left(1 - trans\left(\gamma, \gamma_0 - \frac{\Delta\gamma}{2}, \Delta\gamma\right)\right).$$

$$trans\left(\gamma, \gamma_0 - \frac{\Delta\gamma}{2}, \Delta\gamma\right)$$

is the transition function. Suppose $\Delta\gamma = b$ and $$\gamma_0 - \frac{\Delta\gamma}{2} = a,$$

then, $$trans(\gamma, a, b) = f\left(\frac{\gamma - \left(a - \frac{b}{2}\right)}{b}\right) = f(x)$$

wherein, $f(x)$ is a differentiable function and when its independent variable varies from 0 to 1, the function value varies from 0 to 1 and satisfies $f(x) + f(1-x) = 1$, for example, a differentiable function $f(x) = 3*x^2 - 2*x^3$.

The process of performing image reconstruction using the method for image reconstruction described herein under a helical scan is described below using a detector of 16 rows as an example.

Suppose that the pitch of the helical scan is 9.

Figure 5:
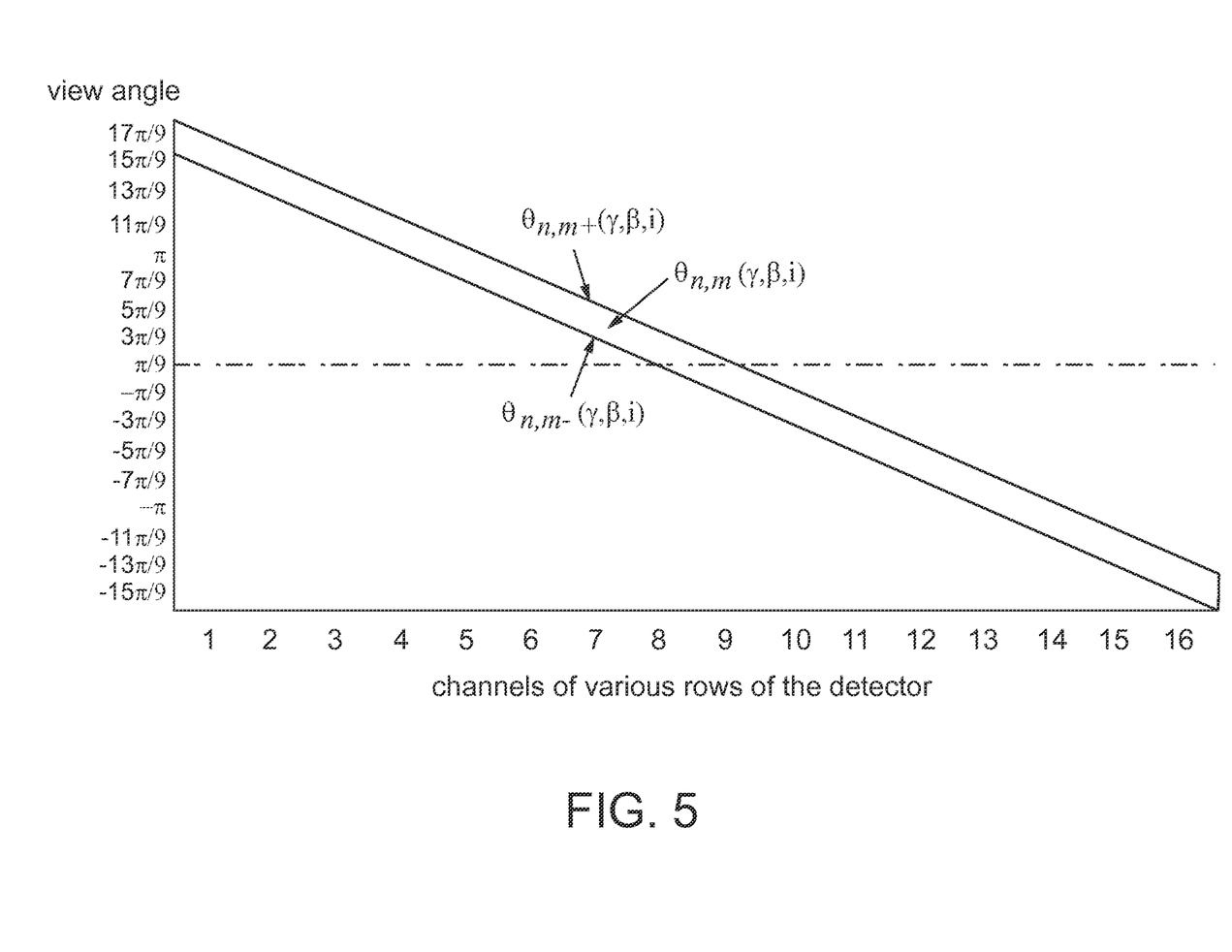
FIG. 5 illustrates a schematic diagram of the convolution reconstruction algorithm/generalized helical interpolation algorithm.

As shown in FIG. 5, the horizontal coordinate represents the rows of the detector and the vertical coordinate represents the view angle $\beta$, and in the horizontal coordinate direction, each row includes a plurality of channels (e.g. 888 channels). FIG. 5 is cited from U.S. Pat. No. 6,873,676.

In this example, data of 16 rows are divided into 8 subsets, each including data of 9 rows. The weight of each subset is $\alpha(n)$, $\Sigma\alpha(n) = 1$.

Figure 6:
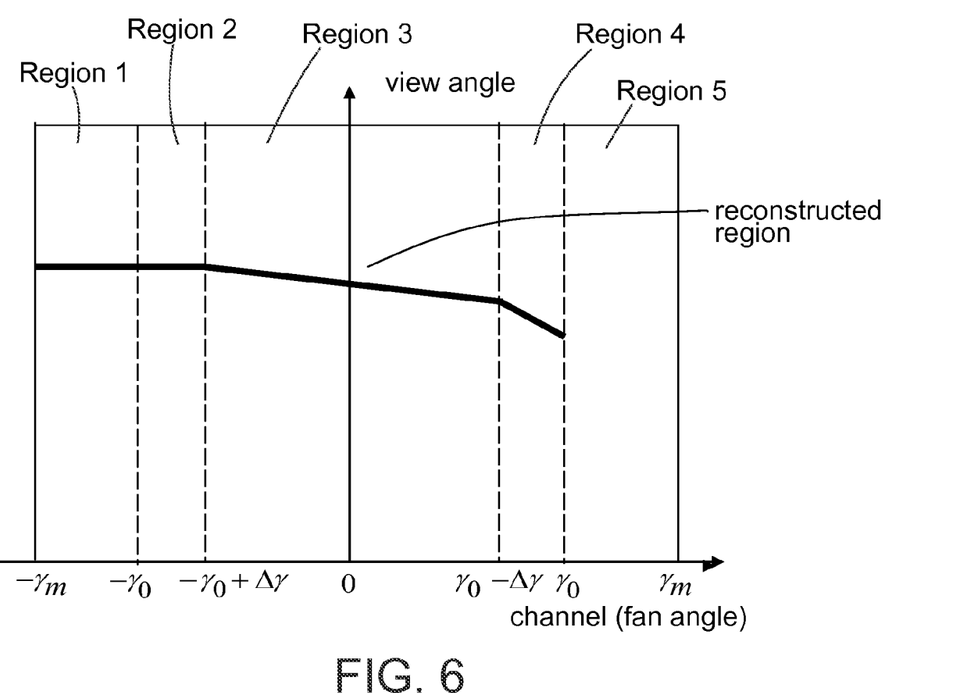
FIG. 6 illustrates a schematic diagram of the axial positions of the asymmetric reconstruction regions in a helical scan.

Likewise, the projection data of the detector of 16 rows are also divided into five regions, as shown in FIG. 2. The reconstructed area is depicted by the thick line in FIG. 6 in the sinusoidal space of the projection data. FIG. 6 depicts the positions of the view angles when the reconstructed area corresponds to various channels in a certain row of the detector. In Region 3, the reconstructed area is a slope line whose slope is $\delta_m$ so as to apply the generalized helical interpolation algorithm. In Region 1 and Region 2, the reconstructed area is a horizontal line that maintains the view angle value at the rightmost end of the reconstructed area in Region 3. In Region 4, the reconstructed area is a slope line whose slope is 2. This helps to reduce the deviation of the reconstructed image slice from the cross-section in the axial direction, and it would be more meaningful to limit the span of the reconstructed area of Regions 1 and 2 in the axial direction, because the larger the span of the reconstructed area in the view angle direction is, the larger the span of the reconstructed area in the axial direction is. As a result, the greater the deviation of the reconstructed image slice from the cross-section is. Meanwhile, Regions 1 and 2 have greater weights. The weight of Region 5 is 0, and the weight in Region 4 also gradually becomes 0.

After dividing the projection data into five regions, the view angle weighting is performed. The weights of Region 5 are 0, and the weights of the remaining four regions are calculated as follows.

For Regions 3 and 1, the formula below is used:

$$w_n(\gamma, \beta, i) = \begin{cases} \sum_{m=1}^{M} \frac{\lambda_{n,m} * (\beta - \theta_{n,m-}(\gamma, \beta, i))}{\theta_{n,m}(\gamma, \beta, i) - \theta_{n,m-}(\gamma, \beta, i)}, & \theta_{n,m-}(\gamma, \beta, i) \le \beta < \theta_{n,m}(\gamma, \beta, i) \\ \sum_{m=1}^{M} \frac{\lambda_{n,m} * (\theta_{n,m+}(\gamma, \beta, i) - \beta)}{\theta_{n,m+}(\gamma, \beta, i) - \theta_{n,m}(\gamma, \beta, i)}, & \theta_{n,m}(\gamma, \beta, i) \le \beta < \theta_{n,m+}(\gamma, \beta, i) \\ 0, & \text{otherwise}, \end{cases}$$

For Region 3, the weights in the subset are calculated by the generalized helical interpolation algorithm, and interpolation is performed between conjugate projections.

$$\theta_{n,m-}(\gamma, \beta, i) = \phi_{i,m} - \frac{\pi}{p} - (2 - \delta_m) * \gamma,$$

$$\theta_{n,m+}(\gamma, \beta, i) = \phi_{i,m} + \frac{\pi}{p} - (2 - \delta_m) * \gamma,$$

$$\theta_{n,m}(\gamma, \beta, i) = \phi_{i,m} - \delta_m * \gamma$$

wherein, $$\phi_{i,m} = \frac{2i\pi}{p},$$

$\phi_{i,m}$ represents the center of the view angle of the central channel in the $i^{th}$ row; and $\delta_m$ is the inclined slope of the $m^{th}$ kind of interpolation (see U.S. Pat. No. 6,873,676).

For Region 1, interpolation between rows is used for the weights in the subset:

$$\theta_{n,m}(\gamma, \beta, i) = \theta_{n,m}(-\gamma_0 + \Delta\gamma, \beta, i) = \phi_{i,m} - \delta_m * (-\gamma_0 + \Delta\gamma)$$

$$\theta_{n,m-}(\gamma, \beta, i) = \theta_{n,m}(-\gamma_0 + \Delta\gamma, \beta, i) - \frac{2\pi}{p} = \phi_{i,m} - \delta_m * (-\gamma_0 + \Delta\gamma) - \frac{2\pi}{p},$$

$$\theta_{n,m+}(\gamma, \beta, i) = \theta_{n,m}(-\gamma_0 + \Delta\gamma, \beta, i) + \frac{2\pi}{p} = \phi_{i,m} - \delta_m * (-\gamma_0 + \Delta\gamma) + \frac{2\pi}{p}.$$

wherein $\gamma_0$ represents the largest fan angle at the small fan angle side; and $\Delta\gamma$ represents the width of the transition region.

The center of view angle of the interpolation function in Region 1 is just the center of a view angle of the corresponding interpolation function in the end of Region 3 that is close to Region 1.

For Region 2, the interpolation transits from the interpolation between rows in Region 1 to the conjugate interpolation of Region 3 along a horizontal direction:

$$w_n(\gamma, \beta, i) = w_n(-\gamma_0, \beta, i) +$$
$$(w_n(-\gamma_0 + \Delta\gamma, \beta, i) - w_n(-\gamma_0, \beta, i)) * trans\left(\gamma, -\gamma_0 + \frac{\Delta\gamma}{2}, \Delta\gamma\right)$$

wherein, $$trans\left(\gamma, -\gamma_0 + \frac{\Delta\gamma}{2}, \Delta\gamma\right)$$

is the transition function. Suppose $\Delta\gamma=b$ and $$-\gamma_0 + \frac{\Delta\gamma}{2} = a,$$

then, $$trans(\gamma, a, b) = f\left(\frac{\gamma - \left(a - \frac{b}{2}\right)}{b}\right), \text{ and } f(x) = 3 * x^2 - 2 * x^3$$

wherein $w_n(-\gamma_0,\beta,i)$ can be calculated from the weight formula of Region 1; and
$w_n(-\gamma_0+\Delta\gamma,\beta,i)$ can be calculated from the weight formula of Region 3.

For Region 4, the interpolation transits from the conjugate interpolation of Region 3 to the 0 contribution of Region 5 along the direction of the declined line shown in FIG. 6:

$$w_n(\gamma, \beta, i) =$$
$$w_n(\gamma_0 - \Delta\gamma, \beta + 2 * (\gamma - \gamma_0 + \Delta\gamma), i) * \left(1 - trans\left(\gamma, \gamma_0 - \frac{\Delta\gamma}{2}, \Delta\gamma\right)\right)$$

wherein $w_n(\gamma_0-\Delta\gamma,\beta+2*(\gamma-\gamma_0+\Delta\gamma),i)$ can be calculated from the weight formula of Region 3.

Figure 7:
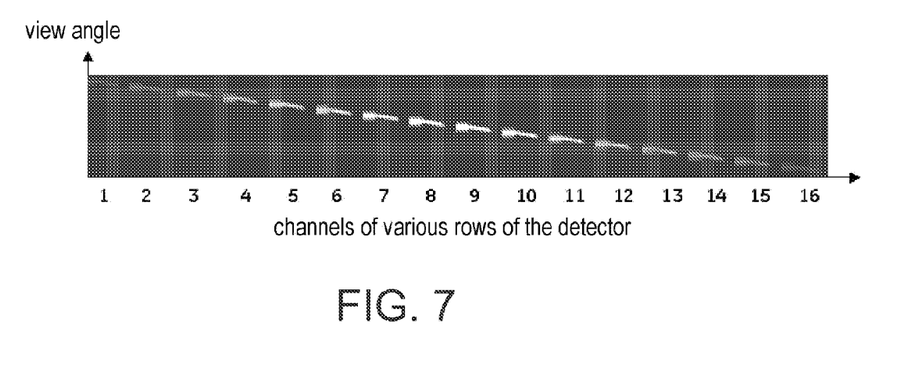
FIG. 7 illustrates a schematic diagram of the weights of the asymmetric reconstruction in a helical scan.

The finally obtained weights of projection data are as shown in FIG. 7. In FIG. 7, there are 16 blocks in the column direction, each block representing one row, and in each block, the column direction is the channel (fan angle) direction, while the vertical direction is the view angle direction.

Then, the projection data are weighted according to the obtained weights. Finally, the tomographic image of the irradiated subject is reconstructed according to the weighted projection data.

Figure 8:
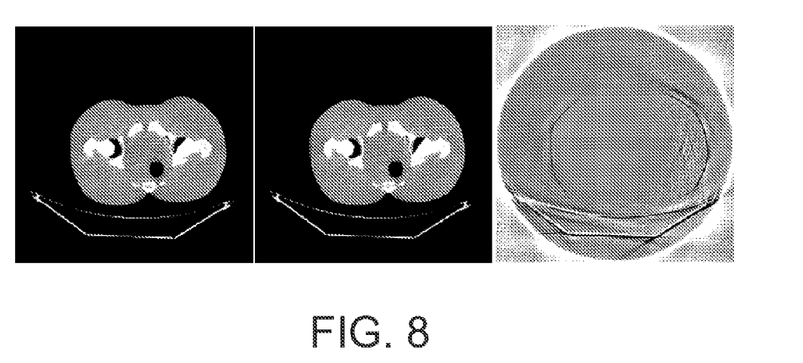
FIG. 8 illustrates a schematic diagram of the result of reconstruction in a helical scan.

As shown in FIG. 8, the leftmost part is the image reconstructed from the projection data obtained by the symmetric detector, the middle part is the image reconstructed from the projection data obtained by the asymmetric detector of this example by using the method for image reconstruction described herein, and the rightmost part is the image of the difference image of the two images. The left two images have a window width of 200 and a window level of 20; and the rightmost image has a window width of 50 and a window level of 0. The centers of all images are in the center of scan. In this example, there are 888 channels in the symmetrical condition, while the asymmetric detector has 444 channels in the left and 362 channels in the right.

As can be seen from FIG. 8, the image (the middle image) reconstructed by the method for image reconstruction described above has almost the same quality in the central region as the image reconstructed by the symmetric detector.

According to another aspect, an apparatus for image reconstruction is provided, which is used for image reconstruction according to the projection data obtained by the asymmetric detector. The apparatus includes a region dividing unit configured to divide the projection data into five regions: region 1, region 2, region 3, region 4 and region 5, wherein Region 1 is an asymmetric region where there are detecting channels but no detecting channels symmetrical about the central channel, Region 2 is a transition region where there are detecting channels, and there are also detecting channels symmetrical about the central channel, Region 3 is a symmetric region where there are detecting channels, and there are also detecting channels symmetrical about the central channel, Region 4 is a transition region where there are detecting channels, and there are also detecting channels symmetrical about the central channel, and Region 5 is a truncated region where there are no detecting channels. The apparatus further includes a view angle weighting unit configured to perform view angle weightings on the projection data in each of the five regions and a reconstructing unit configured to reconstruct the tomographic image of the irradiated subject from the weighted projection data.

For an axial scan, the weights of the projection data in the five regions are as follows: the weights of projection data in Region 1 are 1; the weights of projection data in Region 3 are ½; the weights of projection data in Region 5 are 0; the weights of projection data in Region 2 are 1~½; and the weights of projection data in Region 4 are ½~0.

The weights of projection data in Region 2 are obtained from the following formula:

$$w(\gamma) = 1 - \frac{1}{2} * trans\left(\gamma, -\gamma_0 + \frac{\Delta\gamma}{2}, \Delta\gamma\right)$$

wherein, $w(\gamma)$ represents the weight of projection data obtained when the fan angle is $\gamma$; $\gamma_0$ represents the largest fan angle at the small fan angle side; $\Delta\gamma$ represents the width of the transition region;

$$trans\left(\gamma, -\gamma_0 + \frac{\Delta\gamma}{2}, \Delta\gamma\right)$$

is the transition function. Suppose $\Delta\gamma=b$ and $$-\gamma_0 + \frac{\Delta\gamma}{2} = a,$$

then, $$trans(\gamma, a, b) = f\left(\frac{\gamma - \left(a - \frac{b}{2}\right)}{b}\right) = f(x)$$

wherein, $f(x)$ is a differentiable function, and when $f(x)$'s independent variable varies from 0 to 1, the function value varies from 0 to 1 and satisfies $f(x)+f(1-x)=1$.

The weights of the projection data in Region 4 are obtained from the following formula:

$$w(\gamma) = \frac{1}{2} - \frac{1}{2} * trans\left(\gamma, \gamma_0 - \frac{\Delta\gamma}{2}, \Delta\gamma\right)$$

$$trans\left(\gamma, \gamma_0 - \frac{\Delta\gamma}{2}, \Delta\gamma\right)$$

is the transition function. Suppose $\Delta\gamma=b$ and $$\gamma_0 - \frac{\Delta\gamma}{2} = a,$$

then, $$trans(\gamma, a, b) = f\left(\frac{\gamma - \left(a - \frac{b}{2}\right)}{b}\right) = f(x)$$

wherein, $f(x)$ is a differentiable function, and when $f(x)$'s independent variable varies from 0 to 1, the function value varies from 0 to 1 and satisfies $f(x)+f(1-x)=1$.

For a helical scan, the weights of the projection data in the five regions are as follows: the weights of the projection data in Region 5 are 0; and the weights of the projection data in the remaining four regions are:

$$\xi(\gamma, \beta, i) = \sum_{n=0}^{N-k} \alpha(n) w_n(\gamma, \beta, i)$$

wherein, $\xi(\gamma,\beta,i)$ represents the weight of the projection data at the position of fan angle $\gamma$ in the $i^{th}$ row of the asymmetric detector under the view angle $\beta$; N represents the number of rows of the asymmetric detector, k represents consecutive k rows in the asymmetric detector and k=p, p represents the pitch, a(n) represents the weight of subset n and $\Sigma a(n)=1$, $w_n(\gamma,\beta,i)$ represents, in subset n, the weight of the projection data at the position of fan angle $\gamma$ in the $i^{th}$ row of the asymmetric detector under the view angle $\beta$.

For Region 3 and Region 1:

$$w_n(\gamma, \beta, i) =$$

$$\begin{cases} \sum_{m=1}^{M} \frac{\lambda_{n,m} * (\beta - \theta_{n,m-}(\gamma, \beta, i))}{\theta_{n,m}(\gamma, \beta, i) - \theta_{n,m-}(\gamma, \beta, i)}, & \theta_{n,m-}(\gamma, \beta, i) \leq \beta < \theta_{n,m}(\gamma, \beta, i) \\ \sum_{m=1}^{M} \frac{\lambda_{n,m} * (\theta_{n,m+}(\gamma, \beta, i) - \beta)}{\theta_{n,m+}(\gamma, \beta, i) - \theta_{n,m}(\gamma, \beta, i)}, & \theta_{n,m}(\gamma, \beta, i) \leq \beta < \theta_{n,m+}(\gamma, \beta, i) \\ 0, & \text{otherwise,} \end{cases}$$

wherein, $\lambda_{n,m}$ represents the weight of the $m^{th}$ kind of interpolation in the $n^{th}$ subset; $\theta_{n,m}(\gamma,\beta,i)$ represents the center of view angle when calculating the weight $w_n(\gamma,\beta,i)$ in the $n^{th}$ subset under the $m^{th}$ kind of interpolation, and the weight thereof is 1; $\theta_{n,m-}(\gamma,\beta,i)$ represents the lower boundary of the view angle when calculating $w_n(\gamma,\beta,i)$ under the $m^{th}$ kind of interpolation, and the weight thereof is 0; and $\theta_{n,m+}(\gamma,\beta,i)$ represents the upper boundary of the view angle when calculating $w_n(\gamma,\beta,i)$ under the $m^{th}$ kind of interpolation, and the weight thereof is 0.

For Region 3:

$$\theta_{n,m-}(\gamma, \beta, i) = \phi_{i,m} - \frac{\pi}{p} - (2 - \delta_m)\gamma, \text{ and}$$

$$\theta_{n,m+}(\gamma, \beta, i) = \phi_{i,m} + \frac{\pi}{p} - (2 - \delta_m)\gamma$$

$$\theta_{n,m}(\gamma, \beta, i) = \phi_{i,m} - \delta_m * \gamma$$

wherein, $$\phi_{i,m} = \frac{2i\pi}{p},$$

$\phi_{i,m}$ represents the center of view angle of the central channel in the $i^{th}$ row; and $\delta_m$ in is the inclined slope of the $m^{th}$ kind of interpolation.

For Region 1:

$$\theta_{n,m}(\gamma, \beta, i) = \theta_{n,m}(-\gamma_0 + \Delta\gamma, \beta, i) = \phi_{i,m} - \delta_m * (-\gamma_0 + \Delta\gamma)$$

$$\theta_{n,m-}(\gamma, \beta, i) =$$

$$\theta_{n,m}(-\gamma_0 + \Delta\gamma, \beta, i) - \frac{2\pi}{p} = \phi_{i,m} - \delta_m * (-\gamma_0 + \Delta\gamma) - \frac{2\pi}{p},$$

$$\theta_{n,m+}(\gamma, \beta, i) = \theta_{n,m}(-\gamma_0 + \Delta\gamma, \beta, i) + \frac{2\pi}{p} = \phi_{i,m} - \delta_m * (-\gamma_0 + \Delta\gamma) + \frac{2\pi}{p}$$

wherein $\gamma_0$ represents the largest fan angle at the small fan angle side; and $\Delta\gamma$ represents the width of the transition region.

For Region 2:

$$w_n(\gamma, \beta, i) = w_n(-\gamma_0, \beta, i) +$$

$$(w_n(-\gamma_0 + \Delta\gamma, \beta, i) - w_n(-\gamma_0, \beta, i)) * trans\left(\gamma, -\gamma_0 + \frac{\Delta\gamma}{2}, \Delta\gamma\right)$$

wherein $$trans\left(\gamma, -\gamma_0 + \frac{\Delta\gamma}{2}, \Delta\gamma\right)$$

is the transition function. Suppose $\Delta\gamma=b$ and $$-\gamma_0 + \frac{\Delta\gamma}{2} = a,$$

then, $$trans(\gamma, a, b) = f\left(\frac{\gamma - \left(a - \frac{b}{2}\right)}{b}\right) = f(x)$$

wherein $f(x)$ is a differentiable function and when $f(x)$'s independent variable varies from 0 to 1, the function value varies from 0 to 1 and satisfies $f(x)+f(1-x)=1$.

For Region 4:

$$w_n(\gamma, \beta, i) =$$

$$w_n(\gamma_0 - \Delta\gamma, \beta + 2*(\gamma - \gamma_0 + \Delta\gamma), i) * \left(1 - trans\left(\gamma, \gamma_0 - \frac{\Delta\gamma}{2}, \Delta\gamma\right)\right).$$

The technical solution of the apparatus for image reconstruction described herein corresponds to the method for image reconstruction described herein, so it will not be described in detail any more herein.

According to another aspect, a CT system is provided, which includes the apparatus for image reconstruction described herein.

While the specific embodiments of the present invention have been described in conjunction with the drawings, those skilled in the art can make many alternatives, modifications and equivalent substitution to the present invention without departing from the principle and spirit of the present invention, so such alternatives, modifications and equivalent substitution are intended to fall within the spirit and scope defined by the appended claims.

What is claimed is:

1. A method for image reconstruction according to projection data obtained by an asymmetric detector, said method comprises:

dividing the projection data into Region 1, Region 2, Region 3, Region 4 and Region 5, Region 1 being an asymmetric region where there are detecting channels but no detecting channels symmetrical about a central channel, Region 2 being a transition region where there are detecting channels and there are also detecting channels symmetrical about the central channel, Region 3 being a symmetric region where there are detecting channels and there are also detecting channels symmetrical about the central channel, Region 4 being a transition region where there are detecting channels and there are also detecting channels symmetrical about the central channel, and Region 5 being a truncated region where there is no detecting channel;

performing a view angle weighting on projection data in each of Region 1, Region 2, Region 3, Region 4, and Region 5, wherein for an axial scan, said performing a view angle weighting further comprises weighting the projection data in the Regions such that weights of the projection data in Region 1 are 1, weights of the projection data in Region 3 are ½, weights of the projection data in Region 5 are 0, weights of the projection data in Region 2 are 1~½, and weights of the projection data in Region 4 are ½~0; and reconstructing a tomographic image of an irradiated subject from the weighted projection data.

2. The method for image reconstruction according to claim 1 further comprising obtaining the weights of the projection data in Region 2 from:

$$w(\gamma) = 1 - \frac{1}{2} * trans\left(\gamma, -\gamma_0 + \frac{\Delta\gamma}{2}, \Delta\gamma\right)$$

wherein, $w(\gamma)$ represents a weight of projection data obtained when a fan angle is $\gamma$, $\gamma_0$ represents a largest fan angle at a small fan angle side, $\Delta\gamma$ represents a width of the transition region, $$trans\left(\gamma, -\gamma_0 + \frac{\Delta\gamma}{2}, \Delta\gamma\right)$$

is a transition function, and supposing $\Delta\gamma=b$ and $$-\gamma_0 + \frac{\Delta\gamma}{2} = a,$$

then $$trans(\gamma, a, b) = f\left(\frac{\gamma - \left(a - \frac{b}{2}\right)}{b}\right) = f(x),$$

wherein $f(x)$ is a differentiable function, and when an independent variable of $f(x)$ varies from 0 to 1, a function value varies from 0 to 1 and satisfies $f(x)+f(1-x)=1$.

3. The method for image reconstruction according to claim 2, further comprising obtaining the weights of the projection data in Region 4 from:

$$w(\gamma) = \frac{1}{2} - \frac{1}{2} * trans\left(\gamma, \gamma_0 - \frac{\Delta\gamma}{2}, \Delta\gamma\right),$$

wherein $$trans\left(\gamma, \gamma_0 - \frac{\Delta\gamma}{2}, \Delta\gamma\right)$$

is the transition function, and supposing $\Delta\gamma=b$ and $$\gamma_0 - \frac{\Delta\gamma}{2} = a,$$

then $$trans(\gamma, a, b) = f\left(\frac{\gamma - \left(a - \frac{b}{2}\right)}{b}\right) = f(x),$$

wherein $f(x)$ is a differentiable function, and when an independent variable of $f(x)$ varies from 0 to 1, a function value varies from 0 to 1 and satisfies $f(x)+f(1-x)=1$.

4. The method for image reconstruction according to claim 1, wherein for a helical scan, said performing a view angle weighting further comprising weighting the projection data in the Regions such that weights of the projection data in Region 5 are 0 and weights of the projection data in Region 1, Region 2, Region 3, and Region 4 are:

$$\xi(\gamma, \beta, i) = \sum_{n=0}^{N-k} \alpha(n) w_n(\gamma, \beta, i)$$

wherein $\xi(\gamma,\beta,i)$ represents a weight of the projection data at a position of a fan angle $\gamma$ in an $i^{th}$ row of an asymmetric detector under a view angle $\beta$, N represents a number of rows of the asymmetric detector, k represents consecutive k rows in the asymmetric detector and k=p, p represents the pitch, a(n) represents a weight of a subset n and $\Sigma a(n)=1$, $w_n(\gamma,\beta i)$ represents a weight of the projection data at a position of the fan angle $\gamma$ in the $i^{th}$ row of the asymmetric detector under the view angle $\beta$ in the subset n.

5. The method for image reconstruction according to claim 4, wherein for Region 3 and Region 1:

$$w_n(\gamma, \beta, i) =$$

$$\begin{cases} \sum_{m=1}^{M} \frac{\lambda_{n,m} * (\beta - \theta_{n,m-}(\gamma, \beta, i))}{\theta_{n,m}(\gamma, \beta, i) - \theta_{n,m-}(\gamma, \beta, i)}, & \theta_{n,m-}(\gamma, \beta, i) \le \beta < \theta_{n,m}(\gamma, \beta, i) \\ \sum_{m=1}^{M} \frac{\lambda_{n,m} * (\theta_{n,m+}(\gamma, \beta, i) - \beta)}{\theta_{n,m+}(\gamma, \beta, i) - \theta_{n,m}(\gamma, \beta, i)}, & \theta_{n,m}(\gamma, \beta, i) \le \beta < \theta_{n,m+}(\gamma, \beta, i), \\ 0, & \text{otherwise} \end{cases}$$

wherein $\lambda_{n,m}$ represents a weight in an $n^{th}$ subset with an $m^{th}$ kind of interpolation, $\theta_{n,m}(\gamma,\beta,i)$ represents a center of a view angle when calculating a weight $w_n(\gamma,\beta,i)$ in the $n^{th}$ subset under the $m^{th}$ kind of interpolation and a weight thereof is 1, $\theta_{n,m-}(\gamma,\beta,i)$ represents a lower boundary of the view angle when calculating the weight $w_n(\gamma,\beta,i)$ under the $m^{th}$ kind of interpolation and a weight thereof is 0, and $\theta_{n,m+}(\gamma,\beta,i)$ represents an upper boundary of the view angle when calculating the weight $w_n(\gamma,\beta,i)$ under the $m^{th}$ kind of interpolation and a weight thereof is 0.

6. The method for image reconstruction according to claim 5, wherein for Region 3:

$$\theta_{n,m-}(\gamma, \beta, i) = \phi_{i,m} - \frac{\pi}{p} - (2 - \delta_m) * \gamma,$$

$$\theta_{n,m+}(\gamma, \beta, i) = \phi_{i,m} + \frac{\pi}{p} - (2 - \delta_m) * \gamma,$$

$$\theta_{n,m}(\gamma, \beta, i) = \phi_{i,m} - \delta_m * \gamma$$

wherein $\phi_{i,m} \frac{2i\pi}{p}$, $\phi_{i,m}$ represents a center of a view angle of the central channel in the $i^{th}$ row, and $\delta_m$ is an inclined slope of the $m^{th}$ kind of interpolation.

7. The method for image reconstruction according to claim 6, wherein for Region 1:

$$\theta_{n,m}(\gamma, \beta, i) = \theta_{n,m}(-\gamma_0 + \Delta\gamma, \beta, i) = \phi_{i,m} - \delta_m * (-\gamma_0 + \Delta\gamma)$$

$$\theta_{n,m-}(\gamma, \beta, i) = \theta_{n,m}(-\gamma_0 + \Delta\gamma, \beta, i) - \frac{2\pi}{p} = \phi_{i,m} - \delta_m * (-\gamma_0 + \Delta\gamma) - \frac{2\pi}{p},$$

$$\theta_{n,m+}(\gamma, \beta, i) = \theta_{n,m}(-\gamma_0 + \Delta\gamma, \beta, i) + \frac{2\pi}{p} = \phi_{i,m} - \delta_m * (-\gamma_0 + \Delta\gamma) + \frac{2\pi}{p}$$

wherein $\gamma_0$ represents a largest fan angle at small fan angle side, and $\Delta\gamma$ represents a width of the transition region.

8. The method for image reconstruction according to claim 7, wherein for Region 2:

$$w_n(\gamma, \beta, i) = w_n(-\gamma_0, \beta, i) +$$

$$(w_n(-\gamma_0 + \Delta\gamma, \beta, i) - w_n(-\gamma_0, \beta, i)) * trans\left(\gamma, -\gamma_0 + \frac{\Delta\gamma}{2}, \Delta\gamma\right)$$

wherein $trans\left(\gamma, -\gamma_0 + \frac{\Delta\gamma}{2}, \Delta\gamma\right)$ is a transition function, and supposing $\Delta\gamma=b$ and $$-\gamma_0 + \frac{\Delta\gamma}{2} = a,$$

then $$trans(\gamma, a, b) = f\left(\frac{\gamma - \left(a - \frac{b}{2}\right)}{b}\right) = f(x)$$

where $f(x)$ is a differentiable function and when an independent variable of $f(x)$ varies from 0 to 1, a function value varies from 0 to 1 and satisfies $f(x)+f(1-x)=1$.

9. The method for image reconstruction according to claim 8, wherein for Region 4:

$$w_n(\gamma, \beta, i) = w_n(\gamma_0 - \Delta\gamma, \beta + 2*(\gamma - \gamma_0 + \Delta\gamma), i)*\left(1 - trans\left(\gamma, \gamma_0 - \frac{\Delta\gamma}{2}, \Delta\gamma\right)\right).$$

10. An apparatus for image reconstruction used for image reconstruction according to projection data obtained by an asymmetric detector, said apparatus comprises:
a region dividing unit configured to divide the projection data into Region 1, Region 2, Region 3, Region 4 and Region 5, Region 1 being an asymmetric region where there are detecting channels but no detecting channels symmetrical about a central channel, Region 2 being a transition region where there are detecting channels and there are also detecting channels symmetrical about the central channel, Region 3 being a symmetric region where there are detecting channels and there are also detecting channels symmetrical about the central channel, Region 4 being a transition region where there are detecting channels and there are also detecting channels symmetrical about the central channel, and Region 5 being a truncated region where there is no detecting channel;
a view angle weighting unit configured to perform view angle weighting on the projection data in each of Region 1, Region 2, Region 3, Region 4, and Region 5, wherein for an axial scan, weights of the projection data in the Regions are such that weights of the Projection data in Region 1 are 1, weights of the projection data in Region 3 are ½, weights of the projection data in Region 5 are 0, weights of the projection data in Region 2 are 1~½, and weights of the projection data in Region 4 are ½~0; and
a reconstructing unit configured to reconstruct a tomographic image of an irradiated subject from the weighted projection data.

11. The apparatus for image reconstruction according to claim 10, wherein the weights of the projection data in Region 2 are obtained from:

$$w(\gamma) = 1 - \frac{1}{2}*trans\left(\gamma, -\gamma_0 + \frac{\Delta\gamma}{2}, \Delta\gamma\right)$$

wherein, $w(\gamma)$ represents a weight of projection data obtained when a fan angle is $\gamma$, $\gamma_0$ represents a largest fan angle at a small fan angle side, $\Delta\gamma$ represents a width of the transition region, $$trans\left(\gamma, -\gamma_0 + \frac{\Delta\gamma}{2}, \Delta\gamma\right)$$

is a transition function, and supposing $\Delta\gamma=b$ and $$-\gamma_0 + \frac{\Delta\gamma}{2} = a,$$

then $$trans(\gamma, a, b) = f\left(\frac{\gamma - \left(a - \frac{b}{2}\right)}{b}\right) = f(x),$$

wherein $f(x)$ is a differentiable function, and when an independent variable of $f(x)$ varies from 0 to 1, a function value varies from 0 to 1 and satisfies $f(x)+f(1-x)=1$.

12. The apparatus for image reconstruction according to claim 11, wherein the weights of the projection data in Region 4 are obtained from:

$$w(\gamma) = \frac{1}{2} - \frac{1}{2}*trans\left(\gamma, \gamma_0 - \frac{\Delta\gamma}{2}, \Delta\gamma\right),$$

wherein $trans\left(\gamma, -\gamma_0 - \frac{\Delta\gamma}{2}, \Delta\gamma\right)$ is the transition function, and supposing $\Delta\gamma=b$ and $$\gamma_0 - \frac{\Delta\gamma}{2} = a,$$

then $$trans(\gamma, a, b) = f\left(\frac{\gamma - \left(a - \frac{b}{2}\right)}{b}\right) = f(x),$$

wherein $f(x)$ is a differentiable function, and when an independent variable of $f(x)$ varies from 0 to 1, a function value varies from 0 to 1 and satisfies $f(x)+f(1-x)=1$.

13. The apparatus for image reconstruction according to claim 10, wherein for a helical scan, weights of the projection data in the Regions are such that weights of the projection data in Region 5 are 0 and weights of the projection data in Region 1, Region 2, Region 3, and Region 4 are:

$$\xi(\gamma, \beta, i) = \sum_{n=0}^{N-k} \alpha(n) w_n(\gamma, \beta, i)$$

wherein $\xi(\gamma,\beta,i)$ represents a weight of the projection data at a position of a fan angle $\gamma$ in an $i^{th}$ row of an asymmetric detector under a view angle $\beta$, N represents a number of rows of the asymmetric detector, k represents consecutive k rows in the asymmetric detector and k=p, p represents the pitch, a(n) represents a weight of a subset n and $\Sigma a(n)=1$, $w_n(\gamma,\beta,i)$ represents a weight of the projection data at a position of the fan angle $\gamma$ in the $i^{th}$ row of the asymmetric detector under the view angle $\beta$ in the subset n.

14. The apparatus for image reconstruction according to claim 13, wherein for Region 3 and Region 1:

$$w_n(\gamma, \beta, i) = \begin{cases} \sum_{m=1}^{M} \frac{\lambda_{n,m} * (\beta - \theta_{n,m-}(\gamma, \beta, i))}{\theta_{n,m}(\gamma, \beta, i) - \theta_{n,m-}(\gamma, \beta, i)}, & \theta_{n,m-}(\gamma, \beta, i) \le \beta < \theta_{n,m}(\gamma, \beta, i) \\ \sum_{m=1}^{M} \frac{\lambda_{n,m} * (\theta_{n,m+}(\gamma, \beta, i) - \beta)}{\theta_{n,m+}(\gamma, \beta, i) - \theta_{n,m}(\gamma, \beta, i)}, & \theta_{n,m}(\gamma, \beta, i) \le \beta < \theta_{n,m+}(\gamma, \beta, i), \\ 0, & \text{otherwise} \end{cases}$$

wherein $\lambda_{n,m}$ represents a weight in an $n^{th}$ subset with an $m^{th}$ kind of interpolation, $\theta_{n,m}(\gamma,\beta,i)$ represents a center of a view angle when calculating a weight $w_n(\gamma,\beta,i)$ in the $n^{th}$ subset under the $m^{th}$ kind of interpolation and a weight thereof is 1, $\theta_{n,m-}(\gamma,\beta,i)$ represents a lower boundary of the view angle when calculating the weight $w_n(\gamma,\beta,i)$ under the $m^{th}$ kind of interpolation and a weight thereof is 0, and $\theta_{n,m+}(\gamma,\beta,i)$ represents an upper boundary of the view angle when calculating the weight $w_n(\gamma,\beta,i)$ under the $m^{th}$ kind of interpolation and a weight thereof is 0.

15. The apparatus for image reconstruction according to claim 14, wherein for Region 3:

$$\theta_{n,m-}(\gamma, \beta, i) = \phi_{i,m} - \frac{\pi}{p} - (2 - \delta_m) * \gamma,$$

$$\theta_{n,m+}(\gamma, \beta, i) = \phi_{i,m} + \frac{\pi}{p} - (2 - \delta_m) * \gamma,$$

$$\theta_{n,m}(\gamma, \beta, i) = \phi_{i,m} - \delta_m * \gamma$$

wherein $\phi_{i,m} = \frac{2i\pi}{p}$, $\phi_{i,m}$ represents a center of a view angle of the central channel in the $i^{th}$ row, and $\delta_m$ is an inclined slope of the $m^{th}$ kind of interpolation.

16. The apparatus for image reconstruction according to claim 15, wherein for Region 1:

$$\theta_{n,m}(\gamma, \beta, i) = \theta_{n,m}(-\gamma_0 + \Delta\gamma, \beta, i)$$
$$= \phi_{i,m} - \delta_m * (-\gamma_0 + \Delta\gamma)$$

$$\theta_{n,m-}(\gamma, \beta, i) = \theta_{n,m}(-\gamma_0 + \Delta\gamma, \beta, i) - \frac{2\pi}{p}$$
$$= \phi_{i,m} - \delta_m * (-\gamma_0 + \Delta\gamma) - \frac{2\pi}{p}$$

$$\theta_{n,m+}(\gamma, \beta, i) = \theta_{n,m}(-\gamma_0 + \Delta\gamma, \beta, i) + \frac{2\pi}{p}$$
$$= \phi_{i,m} - \delta_m * (-\gamma_0 + \Delta\gamma) + \frac{2\pi}{p},$$

wherein $\gamma_0$ represents a largest fan angle at small fan angle side, and $\Delta\gamma$ represents a width of the transition region.

17. The apparatus for image reconstruction according to claim 16, wherein
for Region 2:

$$w_n(\gamma, \beta, i) =$$
$$w_n(-\gamma_0, \beta, i) + (w_n(-\gamma_0 + \Delta\gamma, \beta, i) -) * trans\left(\gamma, -\gamma_0 + \frac{\Delta\gamma}{2}, \Delta\gamma\right)$$

wherein $$trans\left(\gamma, -\gamma_0 + \frac{\Delta\gamma}{2}, \Delta\gamma\right)$$

is a transition function, and supposing $\Delta\gamma=b$ and $$-\gamma_0 + \frac{\Delta\gamma}{2} = a,$$

then $$trans(\gamma, a, b) = f\left(\frac{\gamma - \left(a - \frac{b}{2}\right)}{b}\right) = f(x),$$

wherein $f(x)$ is a differentiable function and when an independent variable of $f(x)$ varies from 0 to 1, a function value varies from 0 to 1 and satisfies $f(x)+f(1-x)=1$; and
for Region 4:

$$w_n(\gamma, \beta, i) =$$
$$w_n(\gamma_0 - \Delta\gamma, \beta + 2 * (\gamma - \gamma_0 + \Delta\gamma), i) * \left(1 - trans\left(\gamma, \gamma_0 - \frac{\Delta\gamma}{2}, \Delta\gamma\right)\right).$$

18. A CT system for image reconstruction comprising:
a tube configured to emit X-rays toward an object;
a detector system configured to convert X-rays received from said tube into projection data, said detector system comprising at least one symmetric detector and at least one asymmetric detector; and
an apparatus used for image reconstruction according to the projection data obtained by the asymmetric detector, said apparatus comprises:
a region dividing unit configured to divide the projection data into Region 1, Region 2, Region 3, Region 4 and Region 5, Region 1 being an asymmetric region where there are detecting channels but no detecting channels symmetrical about a central channel, Region 2 being a transition region where there are detecting channels and there are also detecting channels symmetrical about the central channel, Region 3 being a symmetric region where there are detecting channels and there are also detecting channels symmetrical about the central channel, Region 4 being a transition region where there are detecting channels and there are also detecting channels symmetrical about the central channel, and Region 5 being a truncated region where there is no detecting channel;
a view angle weighting unit configured to perform view angle weighting on the projection data in each of Region 1, Region 2, Region 3, Region 4, and Region 5, wherein for an axial scan, weights of the projection data in the Regions are such that weights of the projection data in Region 1 are 1, weights of the Projection data in Region 3 are ½, weights of the projection data in Region 5 are 0, weights of the projection data in Region 2 are 1~½, and weights of the projection data in Region 4 are ½~0; and
a reconstructing unit configured to reconstruct a tomographic image of an irradiated subject from the weighted projection data.

\* \* \* \* \*